(12) United States Patent
Linares

(10) Patent No.: US 8,257,444 B2
(45) Date of Patent: Sep. 4, 2012

(54) END SURFACE MOUNTED PLUGS INCORPORATED INTO AN ARTIFICIAL JOINT AND INCLUDING CUSHIONED SOFT PLASTIC BETWEEN OUTER HARDENED PLASTIC LAYERS

(75) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 65 days.

(21) Appl. No.: 12/881,526

(22) Filed: Sep. 14, 2010

(65) Prior Publication Data

US 2011/0071640 A1   Mar. 24, 2011

Related U.S. Application Data

(60) Provisional application No. 61/244,203, filed on Sep. 21, 2009.

(51) Int. Cl.
*A61F 2/30* (2006.01)
*A61F 2/32* (2006.01)
*A61F 2/38* (2006.01)
*A61F 2/40* (2006.01)

(52) U.S. Cl. ............... 623/18.11; 623/19.11; 623/20.11; 623/20.14; 623/22.11; 623/23.51

(58) Field of Classification Search ............... 623/18.11, 623/19.11, 20.11, 20.14, 22.11, 23.41, 23.48, 623/23.51

See application file for complete search history.

(56) References Cited

U.S. PATENT DOCUMENTS

| | | | |
|---|---|---|---|
| 6,258,126 B1 * | 7/2001 | Colleran | 623/20.29 |
| 6,616,697 B2 * | 9/2003 | Sotereanos | 623/23.26 |
| 7,066,958 B2 * | 6/2006 | Ferree | 623/17.12 |
| 7,235,102 B2 | 6/2007 | Ferree et al. | |
| 7,758,653 B2 | 7/2010 | Steinberg | |
| 7,803,193 B2 | 9/2010 | Steinberg | |
| 2004/0024460 A1 | 2/2004 | Ferree | |
| 2004/0254645 A1 * | 12/2004 | Arnin et al. | 623/20.2 |
| 2005/0171604 A1 * | 8/2005 | Michalow | 623/14.12 |
| 2007/0073409 A1 * | 3/2007 | Cooney et al. | 623/20.11 |
| 2009/0210068 A1 | 8/2009 | Zeller et al. | |
| 2010/0023126 A1 | 1/2010 | Grotz | |
| 2010/0185297 A1 | 7/2010 | Steinberg | |

FOREIGN PATENT DOCUMENTS

| | | | |
|---|---|---|---|
| EP | 66092 A1 * | 12/1982 | |
| FR | 2642301 A1 * | 8/1990 | |
| WO | 2009062158 A2 | 5/2009 | |
| WO | 2009108960 A2 | 9/2009 | |

* cited by examiner

*Primary Examiner* — Corrine M McDermott
*Assistant Examiner* — Randy Shay
(74) *Attorney, Agent, or Firm* — Gifford, Krass, Sprinkle, Anderson & Citkowski, P.C.

(57) ABSTRACT

The present invention discloses an implant for use with a joint defining bone having a three dimensional shape and including a first exposed and joint surface defining layer and an inner most and bone mounting layer. The body further has at least one intermediate layer exhibiting a hardness less than either of the exposed layer and the inner most layer such that, upon mounting the body to a conditioned end of a joint defining bone, it provides the dual features of dynamic cushioning support and external wear resistance.

9 Claims, 2 Drawing Sheets

END SURFACE MOUNTED PLUGS INCORPORATED INTO AN ARTIFICIAL JOINT AND INCLUDING CUSHIONED SOFT PLASTIC BETWEEN OUTER HARDENED PLASTIC LAYERS

CROSS REFERENCE TO RELATED APPLICATIONS

The present application claims the benefit of U.S. Provisional Patent Application Ser. No. 61/244,203 filed Sep. 21, 2009.

FIELD OF THE INVENTION

The present invention discloses an end secured (or fused) implant device for use with various knee, elbow, hip, shoulder or other joint applications. More particularly, the present invention teaches a multi-layer joint surface implant for use with such as existing bones and which exhibits a softer plastic layer encased between outer hardened plastic layers, this in order to enhance both cushioning and wear resistance. Additional variants also contemplate constructing the implant of various metal or poly/metal composites and which maximize the durability and wear resistant aspects of the design.

DESCRIPTION OF THE BACKGROUND ART

The prior art is well documented with examples of knee, elbow, hip, shoulder and other joint applications such as associated with medical implants. An objective associated with such implants is the ability to provide a functional and durable joint which replaces a natural joint which may have become damaged over time.

SUMMARY OF THE PRESENT INVENTION

The present invention discloses an implant for use with a joint defining bone, including a body having a three dimensional shape and including a first exposed and joint surface defining layer and an inner most and bone mounting layer. The body further has at least one intermediate layer exhibiting a hardness less than either of the exposed layer and the inner most layer such that, upon mounting the body to a conditioned end of a joint defining bone, it provides the dual features of dynamic cushioning support and external wear resistance.

Additional features include the body being constructed of at least one of a metal, plastic or composite material. The inner mounting layer further includes an inner marrow contacting portion configured as a perimeter enclosing and inserting portion which engages an opposing and inner facing wall surfaces of the bone. The inner most surfaces of the marrow contacting portions exhibit roughened portions which facilitate bonding of the plug to a previously sectioned/reconditioned bone end.

The exposed and joint defining surface layer further include a contoured profile, with the intermediate layer further having a perimeter edge extending and inner concave profile facilitating dynamic cushioning movement and support of the exposed and joint surface defining layer. The intermediate layer may further include at least one of an undulating and a planar extending width.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

As previously described, the present invention discloses an end secured (this also including fused) implant device for use with various knee, elbow, hip, shoulder or other joint applications. More particularly, the present invention teaches a multi-layer joint surface implant for use with such as existing bones and which in one non-limiting application exhibits a softer plastic layer encased between outer (upper and lower) hardened plastic layers in order to enhance both cushioning and wear resistance. Additional variants also contemplate constructing the implant of various metal or poly/metal composites and which maximize the durability and wear resistant aspects of the design.

Prior to providing a detailed description of joint applications illustrated herein in cutaway, it is understood that they do not include the illustration of such additional components as ligaments, tendons and the like which complete a given joint application and which are understood to be both provided and installed according to known methods and techniques associated with the relevant art. That said, the present invention contemplates the provision of any suitable natural or synthetic ligaments and tendons, and which can further include both existing structure as well as that which can be retrofit designed and/or installed.

Figure 1:
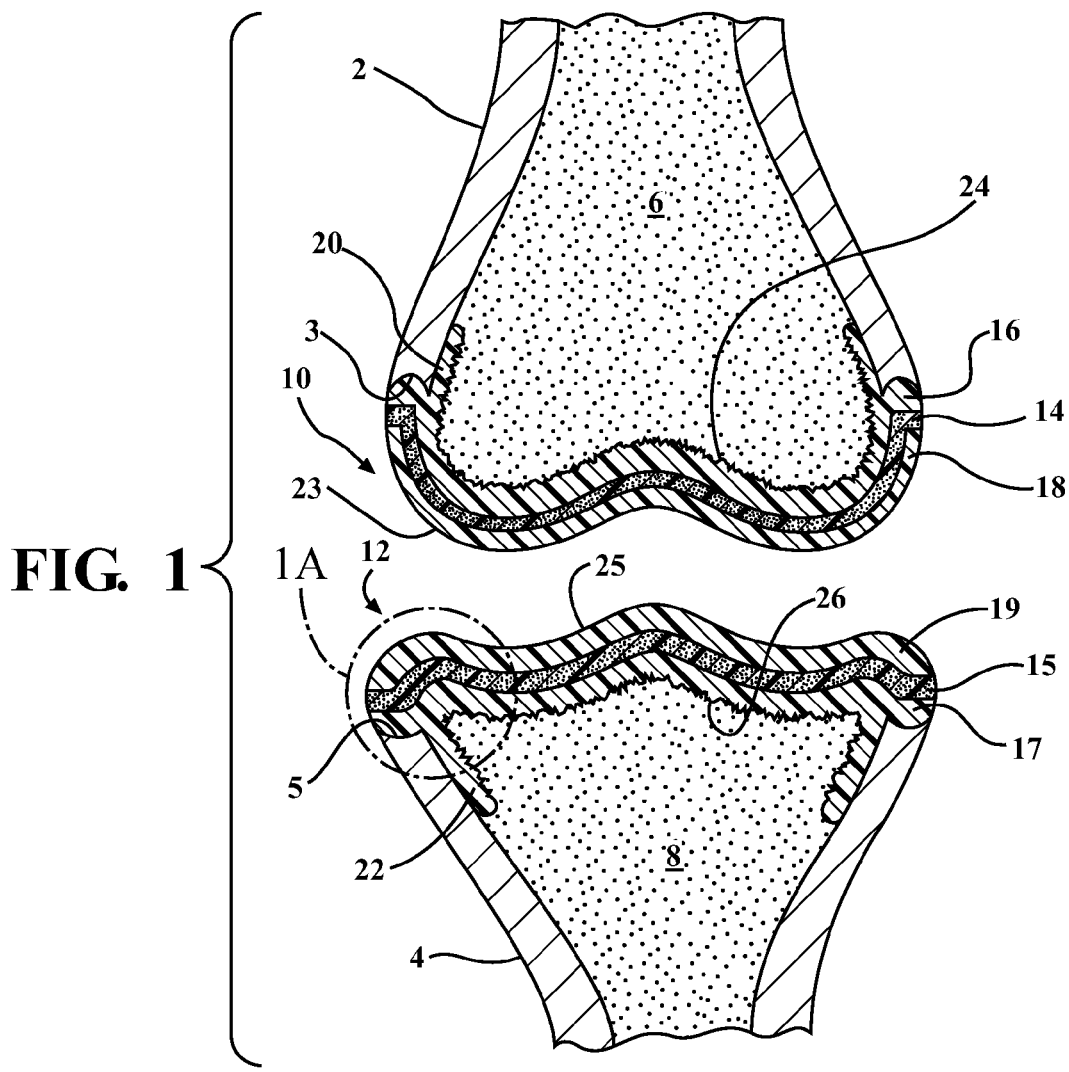
FIG. 1 is a cutaway illustration of a knee joint application and illustrating first and second opposing and respective end surface affixed multi-layered wear and cushioning plugs mounted to reconditioned and opposing ends of first and second joint defining bones.
Figure 1A:
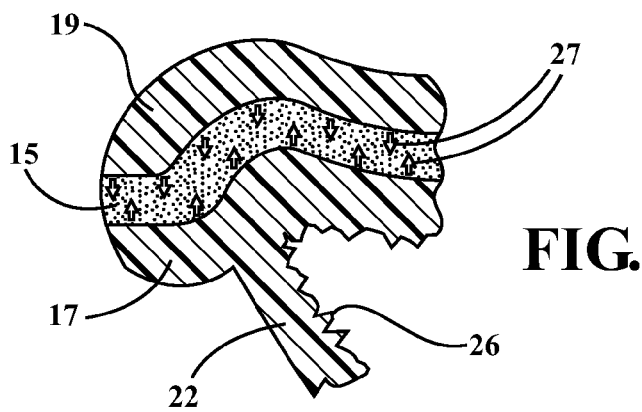
FIG. 1A is an enlarged inset view of a portion of a lower selected wear plug and illustrating the compressive aspect of the outer hardened layers relative to the softer inner sandwiched layer.

Referring again to FIG. 1, as well as to FIG. 1A, a first selected knee joint application is illustrated and in which first and second opposing and respective end surface affixed multi-layered wear and cushioning plugs, or three dimensional shaped bodies, are generally shown by upper plug 10 and lower plug 12 respectively, and which are mounted to reconditioned and opposing ends of first/upper 2 and second/lower 4 joint defining bones. The present invention contemplates surgical reconditioning of existing joint defining bones, however it is also envisioned that one or more of the joint plug designs of the present invention can also be integrated into an artificial bone incorporated into the overall implant.

Figure 2A:
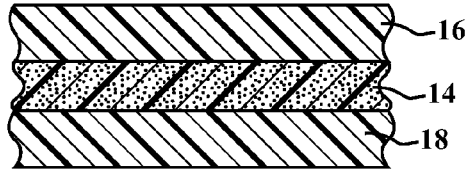
FIGS. 2A and 2B are a pair of lineal cutaway views illustrating the multi layer and inner compressible nature of the joint implantable wear plug.
Figure 2B:
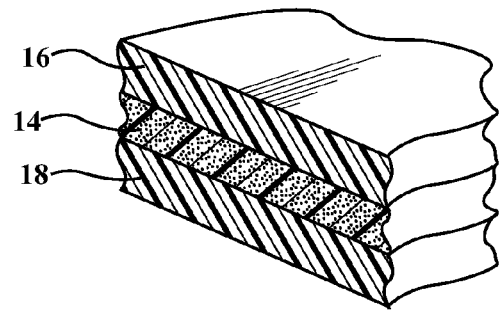

As is also shown in the cutaway views of FIGS. 2A and 2B each plug is constructed as a multi-layer composite and three dimensional shaped article exhibiting a generally planar and typically non-linear pattern having a specified thickness and including a central softer material layer 14 for plug 10 and 15 for plug 12 (such as exhibiting an undulating or non-linear configuration which matches that of an exterior most facing joint defining surface, this further shown at 23 and 25 respectively for plug bodies 10 and 12). Arranged on opposite sides of the central layers 14 and 15 are inner and outer hardened material layers shown at 16 and 18 for plug 10 and at 17 and 19 for plug 12, respectively.

As further shown in FIG. 1, the construction of the inner mounting layers 16 of each plug 10 and 12 can include inwardly perimeter extending and inner marrow contacting portions 20 and 22 extending from the inner layers 16 and 17 and such as likewise shown in cutaway in contact with each of upper 2 and lower 4 bones. The contacting portions 20 and 22 may be configured as perimeter enclosing and inserting portions which engage both the inner facing wall surfaces of the bones 2 and 4 (proximate the sectioned end locations 3 and 5 of the bones 2 and 4) as well as inner marrow supporting portions 6 and 8.

Inner facing surfaces of the inner layers 16 and 17, in combination with the associated and perimeter edge defining marrow contacting portions 20 and 22, each exhibit roughened portions, further depicted at 24 and 26, and which facilitate bonding of the plug shaped bodies 10 and 12 to their respective sectioned bone ends 2 and 4. It is also envisioned that a suitable mechanical fastener or chemical adhesive can be employed to secure inwardly facing and annular edge surfaces of the plugs 10 and 12 to the sectioned annular locations 3 and 5. As previously described, the outer facing hardened plastic (or metal/plastic composite) layers 18 each further exhibit a contoured and joint defining surface profile (see again at 23 for upper plug 10 and at 25 for opposing lower plug 12) these generally defining the preferred surface mating contours of each joint defining body which mimics that of the natural joint being replaced.

As previously described, the construction of the plugs 10 and 12 (as well as any of those falling within the disclosure of the present invention) can include any of plastic, metal or composite materials which are produced in multi-layer fashion as shown. As further illustrated, the provision of the central softer layers 14 and 15 of material embedded within each wear plug 10 and 12 results in a degree of cushioning/inner compressive dynamic performance, this contributing to increased cushioning response and durability when installed in a dynamic in situ joint application. This is further represented by the directional arrows 27 shown in the inset view of FIG. 1A (as well as the compressed position of FIG. 2A) and by which each of the inner softer layers 14 and 15 dynamically respond to the exertions of the outer hardened layers 16 & 17 and 18 & 19, and without sacrificing wear resistance in particular in the opposing and abrading wear zone established between the opposing joint defining surfaces 23 and 25, as well as to a lesser extent along the bone securing and affixing zone established by the inner hardened layers 16 and 17.

Figure 3:
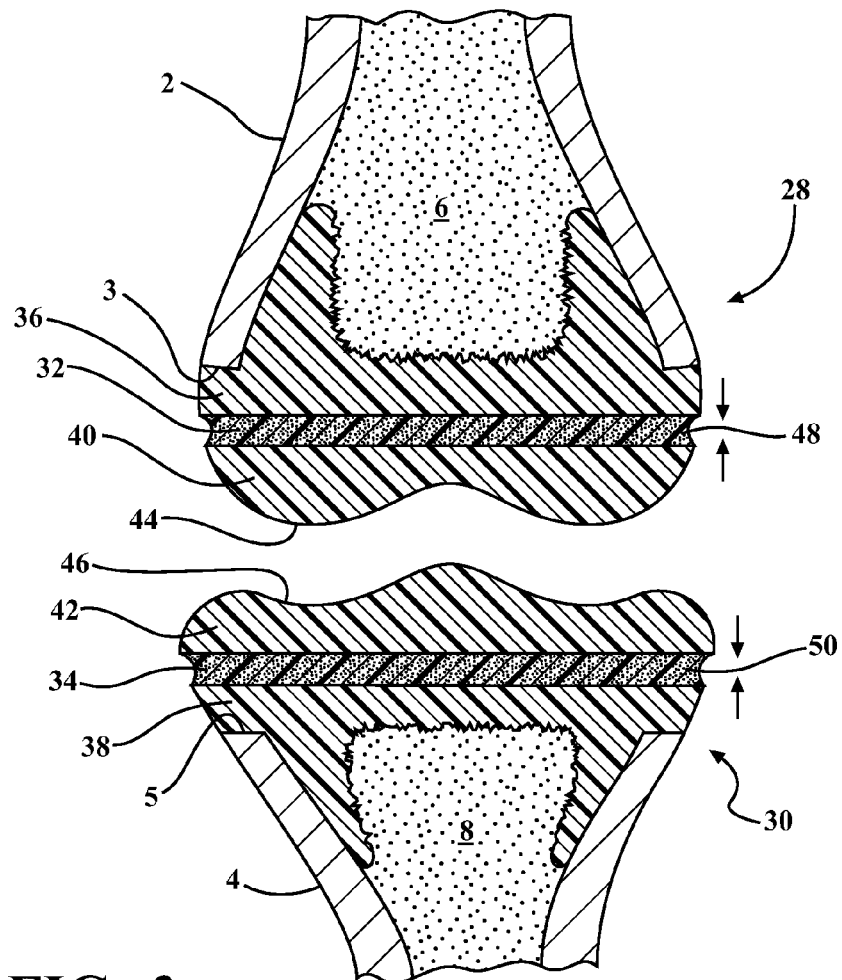
FIG. 3 is a further cutaway illustration of a further version of implantable end surface plugs illustrating substantially planar width extending inner cushioning layers, each of which are sandwiched between an inner-most hardened and bone mounting base and an opposite, outer facing and likewise hardened plastic which can further exhibit a contoured exterior surface for facilitating seating engagement of an opposing plug end surface.

Referring finally to FIG. 3, a further cutaway illustration is shown of a further version of implantable end surface plugs, respectively illustrated by upper and lower plugs at 28 and 30. Each of the plugs are again depicted in cutaway and are understood to each include a substantially planar extending and inner cushioning layer, at 32 and 34 respectively, each of which is sandwiched between an inner-most hardened and bone mounting base layer 36 and 38 and an opposite, outer facing and likewise hardened plastic layer 40 and 42, this further exhibiting a contoured exterior surface profile, at 44 and 46 (and as compared to 23 and 25 in FIG. 1), for facilitating seating engagement of an opposing plug end surface.

The arrangement of FIG. 3 further illustrates an inner edge concave profile or perimeter contour (see at 48 and 50), this further facilitating dynamic cushioning movement and support of the exterior configured hardened plastic layers 40 and 42 relative to the inner and bone/marrow mounted base layers 36 and 38. It is further understood that the dynamic properties of the plugs can be modified, such as by adjusting the hardness/cushion-ability of the inner and/or outer layers.

Although not shown, it is also envisioned that the plugs disclosed herein can be redesigned so as to include multiple alternating layers of hardened/softer material. It is additionally envisioned that the arrangement and pattern of each hard/soft/hard layer interface incorporated into a three dimensional plug design can be modified so as to provide varying dynamic responsiveness to given joint application, and while achieving the dual objectives of maintaining long term durability and wear resistance while at the same time achieving a degree of desired cushioning support within the joint zone. It is further understood that a single plug implant body can be incorporated into a reconditioned and previously damaged bone, this in use with an existing opposing bone exhibiting a natural joint defined surface.

Having described my invention, other and additional preferred embodiments will become apparent to those skilled in the art to which it pertains, and without deviating from the scope of the appended claims.

I claim:

1. An implant for use with at least one of first and second joint defining bones, comprising:
 a plug shaped body comprising at least one of a plastic or plastic/metal composite material, said body having a three dimensional shape and including a first exposed and joint surface defining layer and an inner most layer exhibiting a perimeter enclosing portion configured for mounting over a reconditioned perimeter of the bone;
 said inner most layer further including a roughened contacting portion extending therefrom, configured for being inserted within and simultaneously contacting an inner facing wall surface of the bone and contacting marrow and, in combination with said perimeter enclosing portion, engaging said body to the reconditioned bone; and
 said body further having at least one intermediate layer exhibiting a hardness less than either of said exposed layer and said inner most layer such that, upon mounting said body to the joint defining bone, said body providing the dual features of dynamic cushioning support and external wear resistance.

2. The invention as described in claim 1, said exposed and joint defining surface layer further comprising a contoured profile.

3. The invention as described in claim 1, said intermediate layer further comprising a perimeter edge exhibiting an inner concave profile along its entire length facilitating dynamic cushioning movement and support of said exposed and joint surface defining layer.

4. The invention as described in claim 1, said intermediate layer further comprising at least one of an undulating and a planar extending width.

5. An implant for use with first and second joint defining bones, comprising:
 a first upper plug shaped body and a second lower plug shaped body, each of said bodies having a three dimensional shape and including a first exposed and joint surface defining layer and an inner most layer exhibiting a perimeter enclosing portion configured for mounting over a reconditioned perimeter of an associated bone;
 said inner most layer further including a roughened contacting portion extending therefrom configured for being inserted within and simultaneously contacting an inner facing wall surface of the bone and contacting marrow and, in combination with said perimeter enclosing portion, engaging said body to the reconditioned bone; and each of said bodies further having at least one intermediate layer exhibiting a hardness less than either of said exposed layer and said inner most layer such that, upon mounting each of said bodies to each of the joint defining bones, said bodies provide the dual features of dynamic cushioning support and external wear resistance.

6. The invention as described in claim 5, said bodies each having a specified shape and size and further comprising a plastic or plastic and metal composite material.

7. The invention as described in claim 5, said exposed and joint defining surface layers further comprising a contoured profile.

8. The invention as described in claim 5, each of said intermediate layers further comprising a perimeter edge exhibiting an inner concave profile along its entire length facilitating dynamic cushioning movement and support of said exposed and joint surface defining layer.

9. The invention as described in claim 5, said intermediate layer further comprising at least one of an undulating and a planar extending width.

\* \* \* \* \*